(12) United States Patent
DeGregori

(10) Patent No.: US 6,245,966 B1
(45) Date of Patent: Jun. 12, 2001

(54) ADENOVIRAL MEDIATED GENE TRANSFER INTO LYMPHOCYTES

(75) Inventor: James DeGregori, Denver, CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/272,496

(22) Filed: Mar. 19, 1999

Related U.S. Application Data

(60) Provisional application No. 60/092,782, filed on Jul. 14, 1998.

(51) Int. Cl.[7] .................. C12N 15/09; C12N 15/63; C12N 15/00; C12N 5/00
(52) U.S. Cl. .................. 800/18; 800/3; 800/8; 800/21; 800/22; 800/25; 435/455; 435/456; 435/320.1; 435/325
(58) Field of Search .................. 800/8, 13, 14, 800/18, 3, 21, 22, 25; 435/455, 456, 320.1, 325

(56) References Cited

U.S. PATENT DOCUMENTS 5,162,215 * 11/1992 Bosselman et al. .................. 435/455
5,545,808 * 8/1996 Hew et al. .................. 800/20

FOREIGN PATENT DOCUMENTS

98/11221 3/1998 (WO) .

OTHER PUBLICATIONS

Wall, R. J.Transgenic Livestock: Progress and Prospects for the Future. Theriogenology, vol. 45, pp. 57–68, 1996.*

Mullins et al. Transgenesis in Nonmurine Species. Hypertension, vol. 22, pp. 630–633, Oct. 1993.*

Bergelson, J.M. et al. "Isolation of a Common Receptor for Coxsackie B Viruses and Adenoviruses 2 and 5"; (1997) *Science* 275:1320–1323.

Chu, Y. et al. "Persistent Infection of Human Adenovirus Type 5 in Human Monocyte Cell Lines"; (1992) *Virology* 188:793–800.

Huang, S. et al. "Upregulation of Integrins $\alpha v \beta 3$ and $\alpha v \beta 5$ on Human Monocytes and T Lymphocytes Facilitates Adenovirus–Mediated Gene Delivery"; (1997) *Journal of Virology* 69:2257–2263.

Leon, R.P. et al. "Adenoviral–mediated gene transfer in lymphocytes"; (1998) *Proc. Natl. Acad. Sci. USA* 95:13159–13164.

Miller, A.D. et al. "Improved Retroviral Vectors for Gene Transfer and Expression" (1989) *Biotechniques* 7:980–988.

Nevins, J.R. et al. "Functional Analysis of E2F Transcription Factor"(1997) *Meth. Enzymol* 283:205–219.

Smith et al. "CrmA expression in T lymphocytes of transgenic mice inhibits CD95 (Fas/APO–1)–transduced apoptosis, but does not cause lymphadenopathy or autoimmune disease"; (1996) *EMBO J.* 15:5167–5176.

Wang, X. et al. "Coxsackievirus and Adenovirus Receptor Cytoplasmic and Transmembrane Domains Are Not Essential for Coxsackievirus and Adenorivus Infection"; (1999) *Journal of Virology* 73(3):2559–2562.

Wickham, T.J. et al. "Integrins $\alpha_v \beta_3$ and $\alpha_v \beta_5$ Promote Adenovirus Internalization but Not Virus Attachment"; (1993) *Cell* 73:309–319.

* cited by examiner

*Primary Examiner*—Jill D. Martin
(74) *Attorney, Agent, or Firm*—Greenlee, Winner and Sullivan, P.C.

(57) ABSTRACT

The present application shows that the expression of Coxsackievirus and/or Adenovirus (CAR) in various lymphocyte cell lines is sufficient to facilitate the efficient transduction of these cells by adenoviruses. This property of CAR does not require its cytoplasmic domain. Use of a truncated CAR (tCAR) lacking the cytoplasmic domain has the unexpected advantage in that integrin expression is not increased in lymphocytes expressing tCAR, whereas lymphocytes expressing full-length CAR exhibit upregulated integrin expression. Further provided are transgenic mice which have been genetically engineered for tissue-specific (lymphocyte) expression of tCAR.

3 Claims, 9 Drawing Sheets

SEQUENCE LISTING

<160> NUMBER OF SEQ ID NOS: 7

<210> SEQ ID NO 1
<211> LENGTH: 2434
<212> TYPE: DNA
<213> ORGANISM: Homo sapiens
<220> FEATURE:
<221> NAME/KEY: CDS
<222> LOCATION: (60)..(1154)

<400> SEQUENCE: 1

```
gaattcccag gagcgagagc cgcctacctg cagccgccgc ccacggcacg gcagccacc        59 atg gcg ctc ctg ctg tgc ttc gtg ctc ctg tgc gga gta gtg gat ttc       107
Met Ala Leu Leu Leu Cys Phe Val Leu Leu Cys Gly Val Val Asp Phe
  1               5                  10                  15 gcc aga agt ttg agt atc act act cct gaa gag atg att gaa aaa gcc       155
Ala Arg Ser Leu Ser Ile Thr Thr Pro Glu Glu Met Ile Glu Lys Ala
                 20                  25                  30 aaa ggg gaa act gcc tat ctg ccg tgc aaa ttt acg ctt agt ccc gaa       203
Lys Gly Glu Thr Ala Tyr Leu Pro Cys Lys Phe Thr Leu Ser Pro Glu
             35                  40                  45 gac cag gga ccg ctg gac atc gag tgg ctg ata tca cca gct gat aat       251
Asp Gln Gly Pro Leu Asp Ile Glu Trp Leu Ile Ser Pro Ala Asp Asn
         50                  55                  60 cag aag gtg gat caa gtg att att tta tat tct gga gac aaa att tat       299
Gln Lys Val Asp Gln Val Ile Ile Leu Tyr Ser Gly Asp Lys Ile Tyr
 65                  70                  75                  80 gat gac tac tat cca gat ctg aaa ggc cga gta cat ttt acg agt aat       347
Asp Asp Tyr Tyr Pro Asp Leu Lys Gly Arg Val His Phe Thr Ser Asn
                     85                  90                  95 gat ctc aaa tct ggt gat gca tca ata aat gta acg aat tta caa ctg       395
Asp Leu Lys Ser Gly Asp Ala Ser Ile Asn Val Thr Asn Leu Gln Leu
                100                 105                 110 tca gat att ggc aca tat cag tgc aaa gtg aaa aaa gct cct ggt gtt       443
Ser Asp Ile Gly Thr Tyr Gln Cys Lys Val Lys Lys Ala Pro Gly Val
            115                 120                 125 gca aat aag aag att cat ctg gta gtt ctt gtt aag cct tca ggt gcg       491
Ala Asn Lys Lys Ile His Leu Val Val Leu Val Lys Pro Ser Gly Ala
        130                 135                 140 aga tgt tac gtt gat gga tct gaa gaa att gga agt gac ttt aag ata       539
Arg Cys Tyr Val Asp Gly Ser Glu Glu Ile Gly Ser Asp Phe Lys Ile
145                 150                 155                 160 aaa tgt gaa cca aaa gaa ggt tca ctt cca tta cag tat gag tgg caa       587
Lys Cys Glu Pro Lys Glu Gly Ser Leu Pro Leu Gln Tyr Glu Trp Gln
                165                 170                 175 aaa ttg tct gac tca cag aaa atg ccc act tca tgg tta gca gaa atg       635
Lys Leu Ser Asp Ser Gln Lys Met Pro Thr Ser Trp Leu Ala Glu Met
```

-continued

```
                  180                 185                 190
act tca tct gtt ata tct gta aaa aat gcc tct tct gag tac tct ggg      683
Thr Ser Ser Val Ile Ser Val Lys Asn Ala Ser Ser Glu Tyr Ser Gly
        195                 200                 205 aca tac agc tgt aca gtc aga aac aga gtg ggc tct gat cag tgc ctg      731
Thr Tyr Ser Cys Thr Val Arg Asn Arg Val Gly Ser Asp Gln Cys Leu
    210                 215                 220 ttg cgt cta aac gtt gtc cct cct tca aat aaa gct gga cta att gca      779
Leu Arg Leu Asn Val Val Pro Pro Ser Asn Lys Ala Gly Leu Ile Ala
225                 230                 235                 240 gga gcc att ata gga act ttg ctt gct cta gcg ctc att ggt ctt atc      827
Gly Ala Ile Ile Gly Thr Leu Leu Ala Leu Ala Leu Ile Gly Leu Ile
                245                 250                 255 atc ttt tgc tgt cgt aaa aag cgc aga gaa gaa aaa tat gaa aag gaa      875
Ile Phe Cys Cys Arg Lys Lys Arg Arg Glu Glu Lys Tyr Glu Lys Glu
            260                 265                 270 gtt cat cac gat atc agg gaa gat gtg cca cct cca aag agc cgt acg      923
Val His His Asp Ile Arg Glu Asp Val Pro Pro Pro Lys Ser Arg Thr
        275                 280                 285 tcc act gcc aga agc tac atc ggc agt aat cat tca tcc ctg ggg tcc      971
Ser Thr Ala Arg Ser Tyr Ile Gly Ser Asn His Ser Ser Leu Gly Ser
    290                 295                 300 atg tct cct tcc aac atg gaa gga tat tcc aag act cag tat aac caa     1019
Met Ser Pro Ser Asn Met Glu Gly Tyr Ser Lys Thr Gln Tyr Asn Gln
305                 310                 315                 320 gta cca agt gaa gac ttt gaa cgc act cct cag agt ccg act ctc cca     1067
Val Pro Ser Glu Asp Phe Glu Arg Thr Pro Gln Ser Pro Thr Leu Pro
                325                 330                 335 cct gct aag gta gct gcc cct aat cta agt cga atg ggt gcg att cct     1115
Pro Ala Lys Val Ala Ala Pro Asn Leu Ser Arg Met Gly Ala Ile Pro
            340                 345                 350 gtg atg att cca gca cag agc aag gat ggg tct ata gta tagagcctcc      1164
Val Met Ile Pro Ala Gln Ser Lys Asp Gly Ser Ile Val
        355                 360                 365 atatgtctca tctgtgctct ccgtgttcct ttccttttt tgatatatga aaacctattc     1224
tggtctaaat tgtgttacta gcctcaaaat acatcaaaaa ataagttaat caggaactgt    1284
acggaatata ttttaaaaa tttttgtttg gttatatcga aatagttaca ggcactaaag     1344
ttagtaaaga aagtttacc atctgaaaaa gctggatttt ctttaagagg ttgattataa     1404
agttttctaa atttatcagt acctaagtaa gatgtagcgc tttgaatatg aaatcatagg    1464
tgaagacatg ggtgaactta cttgcatacc aagttgatac ttgaataacc atctgaaagt    1524
ggtacttgat cattttacc attattttta ggatgtgtat ttcatttatt tatgcccac      1584 cagtctcccc caaattagta cagaaatatc catgacaaaa ttacttacgt atgtttgtac    1644
ttggttttac agctcctttg aaaactctgt gtttggaata tctctaaaaa catagaaaac   1704
actacagtgg tttagaaatt actaatttta cttctaagtc attcataaac cttgtctatg    1764
aaatgacttc ttaatatttt agttgataga ctgctacagg taatagggac ttagcaagct    1824 ctttatatg ctaaaggagc atctatcaga ttaagttaga acatttgctg tcagccacat    1884
attgagatga cactaggtgc aatagcaggg atagattttg ttggtgagta gtctcatgcc    1944
ttgagatctg tggtggtctt caaaatggtg gccagccaga tcaaggatgt agtatctcat    2004
agttcccagg tgatatttt cttattagaa aaatattata actcatttgt tgtttgacac    2064
ttatagattg aaatttccta atttattcta aatttaagt ggttctttgg ttccagtgct    2124
ttatgttgtt gttgttttg gatggtgtta catattatat gttctagaaa catgtaatcc    2184
```

-continued

```
taaatttacc ctcttgaata taatccctgg atgatatttt ttatcataaa tgcagaataa    2244
tcaaatacat tttaagcaag ttaagtgtcc tccatcaatt ctgtattcca gacttgggag    2304
gatgtacagt tgctgttgtg tgatcaaaca tgtctctgtg tagttccagc aaatcaagct    2364
gagctttgaa aaagtttgtc ttagttttgt gaaggtgatt tattcttaga aaaaaaaaa     2424 aaaaaaaaaa                                                           2434
```

<210> SEQ ID NO 2
<211> LENGTH: 365
<212> TYPE: PRT
<213> ORGANISM: Homo sapiens

<400> SEQUENCE: 2

```
Met Ala Leu Leu Leu Cys Phe Val Leu Leu Cys Gly Val Val Asp Phe
  1               5                  10                  15

Ala Arg Ser Leu Ser Ile Thr Thr Pro Glu Glu Met Ile Glu Lys Ala
             20                  25                  30

Lys Gly Glu Thr Ala Tyr Leu Pro Cys Lys Phe Thr Leu Ser Pro Glu
         35                  40                  45

Asp Gln Gly Pro Leu Asp Ile Glu Trp Leu Ile Ser Pro Ala Asp Asn
     50                  55                  60

Gln Lys Val Asp Gln Val Ile Ile Leu Tyr Ser Gly Asp Lys Ile Tyr
 65                  70                  75                  80

Asp Asp Tyr Tyr Pro Asp Leu Lys Gly Arg Val His Phe Thr Ser Asn
                 85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Val Leu Val Lys Pro Ser Gly Ala
    130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
            180                 185                 190

Thr Ser Ser Val Ile Ser Val Lys Asn Ala Ser Ser Glu Tyr Ser Gly
        195                 200                 205

Thr Tyr Ser Cys Thr Val Arg Asn Arg Val Gly Ser Asp Gln Cys Leu
    210                 215                 220

Leu Arg Leu Asn Val Val Pro Pro Ser Asn Lys Ala Gly Leu Ile Ala
225                 230                 235                 240

Gly Ala Ile Ile Gly Thr Leu Leu Ala Leu Ala Leu Ile Gly Leu Ile
                245                 250                 255

Ile Phe Cys Cys Arg Lys Lys Arg Arg Glu Glu Lys Tyr Glu Lys Glu
            260                 265                 270

Val His His Asp Ile Arg Glu Asp Val Pro Pro Lys Ser Arg Thr
        275                 280                 285

Ser Thr Ala Arg Ser Tyr Ile Gly Ser Asn His Ser Ser Leu Gly Ser
    290                 295                 300

Met Ser Pro Ser Asn Met Glu Gly Tyr Ser Lys Thr Gln Tyr Asn Gln
305                 310                 315                 320
```

```
Val Pro Ser Glu Asp Phe Glu Arg Thr Pro Gln Ser Pro Thr Leu Pro
                325                 330                 335

Pro Ala Lys Val Ala Ala Pro Asn Leu Ser Arg Met Gly Ala Ile Pro
            340                 345                 350

Val Met Ile Pro Ala Gln Ser Lys Asp Gly Ser Ile Val
        355                 360                 365

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 3
gaattcccag gagcgagagc c                                          21

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 4
cgcagctcga gctacacatc ttccctgata tcgtg                            35

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 5
cgcagctcga gctatccttc catgttggaa gg                               32

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 6
cgcagctcga gctatttacg acagcaaaag atgat                            35

<210> SEQ ID NO 7
<211> LENGTH: 4072
<212> TYPE: DNA
<213> ORGANISM: Mus musculus

<400> SEQUENCE: 7
gaattcagtt gctcgctatc ttatttaaag agccaaatct ggagaagtag accgtagagc   60
acaggttctc aatctgtggg tcgcaacccc tttgggcatc caaaagcact tttagacagg  120
ttgcatatca gatatccagt atatcagata tttatattta aaattattta aaagtcgtag  180
cagtggcaag attacggtta caaagtagca acgaaaataa ttttatgctt gggagtcatc  240
acagcatgag gaaatgagct gtattaacgg gtcccagcat taggaaggct gagaaccact  300
```

-continued

| | |
|---|---|
| gccctaaaga gaagagacag tcaagtgaaa agcagaaagc gaccctgctg tcagttataa | 360 |
| tctgaggagg ggagagttga atattagctg tcagcccacc atgtgcaaac ataaggatgt | 420 |
| ccagttcagc tcaacgggtc atcacagtta atttgtgatg gcgtaccaga cgtatatatt | 480 |
| tgcatactaa cggttccttg gcttggcttg agaatcaccc atccggaaaa agatctgcga | 540 |
| gaccgaggcg gatgaagtta ggtgagaagg ggattgcgag ctggactatg caaagagtat | 600 |
| tcccagaaat ggaccggcgg ctgggctggt gagcccggag gctaatctag caaatttacg | 660 |
| cccccttttg gtcacagcag gagatgcggg ctcaggaccg gcagctggca gggcagctgc | 720 |
| tcaggctgcg ggcccggctg cacagactga aagtggacca agtctgtcac ctgcaccagg | 780 |
| agcttctgga tgaggctgag ctggagatgg agttagagtc tgggactggc ttgcctctgg | 840 |
| ccccaccgct gcggcatctg ggactcacgc gcatgaacat cagtgccaga cgcttcaccc | 900 |
| tctgctgaca gcagacttgg gtgtctcttg cagtatctgg ggagaaagaa ggaaggaaga | 960 |
| gggaccccgg aggctctggc tacctgctgg ggaaggtggg cacacttagg tttccaaaag | 1020 |
| ctgaatttag agagcacagg atggagggga ggaggagagg aaactcgggc cccaaatgtc | 1080 |
| ttaataaaaa atgcattgaa tcccatcaag gtttctgtag actgtcacag agcctaaata | 1140 |
| aatgttgttg tatattcatc ctgtgtcact gggactttag ggattccaca acaggagaca | 1200 |
| agatggcacc aggtgtcccc aacagctccc gatctatttc tctaacttta tcaaaatcaa | 1260 |
| aagtgagaaa aatttaaatg aagatgaaga ttcattgtgt tttttgattg tgtgtgtgac | 1320 |
| cagagaggcc agaaaaggat tagctgagct ggagacacaa gctgttgtaa gctgcctgtt | 1380 |
| gtggatgctg cctacggaac tcaggtcctc tgtgagcagc aaagggcttt ttttctccag | 1440 |
| cccccaaact taaaatcttc tgccattctc atgacaggt gtctaggtaa attgaagact | 1500 |
| tggagaaagc agaaagtggt agttctgtgt catctctgct atttatttat ttttctttt | 1560 |
| tctgttttc tttttttttt cttttctttt tctcttttc cctgatgcag ggtctcacta | 1620 |
| ggtaactccg actgtcctga agcccatact ggccttgaac tcacagagat tcacttgcct | 1680 |
| ccggagtgct ggggttaaag gtgtgcacca ctctgcccgg cttcccctat ttaactctat | 1740 |
| tagacacata gtgggaaaat caggccacta tgaggcagat ctctatgatc ttgacgccag | 1800 |
| tctgctctac agagcgagtt ccaggtcagt aaggaccacc tagaaagaga ccctgtctcc | 1860 |
| aaaaatccaa aaataagcaa acaaacaaat taagaaaaaa acccagctag ttgctaattt | 1920 |
| ttgctccacg ggcagctaga tatgcattac tttagaacac acccgataaa ttcatgcact | 1980 |
| gcttcttagc accgtgcccc ccaggcgggt gctgaagctg aggtgagcag cagtaaaatg | 2040 |
| ctaaggtttc taagtgagga cagcagggcg gtatatcagg tctggagaca catctgccgg | 2100 |
| ctctgtcact ctcagggttg ggttgttttt tttttttttc cttctgtgtg actctcagcc | 2160 |
| tttgtttctg tgtttctctc tttgtctgac tttccaactc agacttcctc ccccccccat | 2220 |
| ttcctgttcc cccttccctc agcagctggg gtgcacacag cttcagctcc tacctcacaa | 2280 |
| acccaacaa tgctctgtgg gctcccctcc ccctgcctgc tcactcagcg tagctcaaga | 2340 |
| ggtgacacat ttacactttc tttccagtga ggtcaggacc cattcttggc cctgataggg | 2400 |
| gccatttggg gttcctcaca tcactggtgg cctggccctc tgcctgtgag ggacacaatc | 2460 |
| ctcatttttg cctgctggca gcttgttgtg gagttcttaa actcctgctg atgtcagaat | 2520 |
| gtctctgcct gccacagata cctgtgcagt atgcttgctc ggtcctctac cggaggcaac | 2580 |
| tcgtggttat ggctatgcgc tccattaggg gtgtggcctt gcctctactt gaattaccat | 2640 |
| tctgctgtgc tgtcctgtcc cctgcctgtt attctatcta tctatctatc tatctatcta | 2700 |

```
tctatctatc tatctatcta tctatctatt atctatctac tatctatcta tatctactat  2760
ctatctatct atctatcttc tatctgtctc tatcatctat gtatctatct gtgtatctct  2820
gtatgtatct atgtttgtat gtatctatct acctatgtat ctatgtatct atctatgtat  2880
ctatgtatct atctctatct atcatctatg tatctatgta tctctgtatg tatatatgta  2940
tgtatgtatg tgtgtatgtg tgtatgtatg tatgtatgtg tgtatctacc tatctatcta  3000
tctacctaca tctatctatc tatctatcta tctatctatc gaaacagggt ctctttatgt  3060
agctctggct gtcctggaac ttactgcata agttagtctg gcctgaaact tgcagagatc  3120
tgccagcctc tgcctccgga atgctgggat taaagtctta tgccaccatg ccccagcctg  3180
tcactagggc cttaagacat gaggttttct tgtcttcctc ctgaaacaga ctgtcaacag  3240
tcgatcctta ggcacaggat gacatggata cggctctgcc agtgaatgtg gctgctgttt  3300
ttactatagt accttgtcac caactatcta acagagatag atactgtcca ggttcaactc  3360
tgaacaagag atgcctttgg ctgtccggct aaattaaagg ccacccagtt cttacatagc  3420
acggctggag ttgagtgcag cgccatttcc ttccctgtga gctaaactgt agctgctgtg  3480
ttctgctcac gggggcaaag gctctctttg gatctcttac ccaggagtat cttggagggt  3540
aggaggagtg ctccatcaaa cagccttccc caccatgttt agtgaccttc acggggagga  3600
agaggcaagt gaatctctgt gagttcaagg caacatagca aattccataa cagtcagggc  3660
gacacggtga gtccctgcgt taaaaaaaag atcctctcat tggttgatga cgacgacgac  3720
gatgatgatg atgattggac ttgaggggtc taggctggtc tggaactctg tatgtagcca  3780
ttcctgtctt cacctccaga acgctgggaa tatggaccta tgccatcaca cacagccttc  3840
ctccctaagt gcctccctca gtatgagtag aagctggcct agagatgtat gggacccaag  3900
aggctgaggg ggtctaggtc tatggcagca ggaagcctga ggtgctggag gcttgtggtt  3960
gggttgctgg ggctgggttg gctgcagagc cctcaggaga caggaagtca gggtggaacg  4020
tgggcgcgag gagacaggtg gtgactacga cggcgagggg agctgacacc gg           4072
```

ADENOVIRAL MEDIATED GENE TRANSFER INTO LYMPHOCYTES

CROSS REFERENCE TO RELATED APPLICATIONS

This application claims priority from U.S. Provisional Application Ser. No. 60/092,782 filed Jul. 14, 1998.

ACKNOWLEDGMENT OF FEDERAL RESEARCH SUPPORT

This invention was made, at least in part, with funding from the National Institutes of Health. Accordingly, the United States Government may have certain rights in this invention.

BACKGROUND OF THE INVENTION

The invention relates to a method of introducing exogenous genetic materials into lymphocytes, in vitro and in vivo, and its use in studying the function and regulation of immune system. Specifically, lymphocytes are genetically engineered to express a truncated Coxsackievirus and/or Adenovirus Receptor (tCAR) protein to allow improved adenovirus vector transfection.

The inefficiency of gene delivery into lymphocytes has hampered the investigation of the pathways that control lymphocyte physiology. Although retrovirus vectors have been used successfully to transduce multiple hematopoietic cell types, experiments involving retroviral transduction of lymphocytes are limited by the difficulty in transducing the entire population of cells, the requirement that the cells be proliferating for viral integration, and the time required for the transduction and expression of the introduced gene. Other approaches to manipulate gene expression in lymphocyte cell lines often require either the generation of cell lines that express the desired gene product, sometimes under the control of an inducible promoter, or the transient transfection of the gene of interest into a fraction of the cells. In addition, the manipulation of gene expression in vivo usually entails the creation of transgenic or gene disrupted mice. These technologies, however, are costly and time consuming, thus have been applied to a few limited cases. Furthermore, the expression of an exogenous gene in transgenic mice is often detrimental to the normal development. The inability to introduce genes easily and efficiently into lymphocytes and examine the consequences of such expression soon after gene delivery limits the characterization of lymphocyte pathways that control cell growth, differentiation and death.

Adenoviral vectors are attractive in that either proliferating or quiescent cells can be transduced, the expression of the introduced gene is evident by as early as 5 hrs after transfection, the vectors can accommodate large insert sizes (7–9 kilobases), and high titer stocks are easily generated [Nevins, J. R. et al., (1997) Meth. Enzymol 283:205–219]. A particular advantage of the adenovirus vectors lies in their ability to transduce the entire cell population. Group C adenovirus (e.g. Ad2 and Ad5) infection requires the high affinity attachment of the viral fiber capsid protein to a cellular receptor and viral penton base binding to certain cellular integrins, followed by cell entry via receptor-mediated endocytosis [Wickham, T. J., et al., (1993) Cell 73:309–319]. Unfortunately, although adenovirus can infect a wide range of cell types, lymphocytes are not very susceptible to adenovirus infection, apparently as a result of the failure of adenovirus to efficiently bind the cell surface and be internalized [DeMatteo, R. P. et al., (1997) Ann. of Surgery 222:229–242; Neering, S. J. et al., (1996) Blood 88:1147–1155; Chu, Y. et al., (1992) Virology 188:793–800]. In part, the inability of adenovirus to enter T cells is due to the very low levels of cellular fiber receptor expressed on these cells [Huang, S. et al., (1997) Journal of Virology 69:2257–2263; Huang, S. et al., (1996) J. Virol. 70:4502–4508]. In addition, T cells express limiting levels of $\alpha V$ containing integrins, and mitogen-mediated upregulation of $\alpha V$ integrin expression confers limited infection by adenovirus vectors [Huang et al., (1997) supra].

The cDNA for the cellular receptor for the adenoviral fiber protein, CAR (for Coxsackievirus and/or Adenovirus Receptor), was recently cloned, and the expression of CAR in Chinese hamster ovary (CHO) cells increased their susceptibility to adenovirus infection approximately 100 fold [Bergelson, J. M. et al., (1997) Science 275:1320–1323].

There has been a long-felt need in the art for an efficient gene transfer method for lymphocytes. The invention described herein provides in vitro cell culture systems and in vivo animal models allowing efficient adenovirus-mediated transduction, and subsequently, enabling the art to study diverse functions of lymphocytes as well as to test agents to modulate lymphocyte activity.

SUMMARY OF THE INVENTION

In the context of the present invention, a truncated form of CAR (tCAR), lacking substantially all of the cytoplasmic domain, has adenovirus and/or Coxsackie virus binding activity but yet no adverse effect on integrin expression when it (tCAR) is expressed in lymphocytes in culture or in vivo. With reference to SEQ ID NO:1, mature human tCAR has an amino acid sequence extending from 1 to between about 262 and 285; as specifically exemplified, mature tCAR has 262 amino acids.

The present invention further provises a method for generating lymphocyte cell lines which are susceptible for adenoviral transduction. Specifically, lymphocytes in vitro are genetically engineered using retroviral expression vectors to express the truncated form of CAR (tCAR) stably and thus become high efficiency target cells for adenoviral transduction.

The present invention also provides a transgenic mouse which expresses truncated CAR in its lymphocytes and is thus susceptible for adenoviral transduction in a tissue specific manner. These animals can be used for targeted gene transfer into lymphocytes using adenoviral vectors in vivo or ex vivo.

BRIEF DESCRIPTION OF THE DRAWINGS

FIG. 4A is a diagram of three different C-terminally truncated mutants of the CAR receptor. Those mutants were generated by PCR amplification using internal primers containing a stop codon immediately following the indicated residue. The predicted transmembrane domain (TM) encompasses residues 236 through 258, as illustrated in the schemata. FIG. 4B shows the expression level of green fluorescent protein (GFP). LXSN retroviruses encoding the CAR truncation (CAR Δ) mutants (or the LXSN and LXSN-CAR as control viruses) which were used to transduce EL-4 cells, and pooled NeoR cells were selected. The CAR Δ1 #6 cell clone was derived from a single cell sorted from the highly fluorescent cells resulting from AdCMV-GFP transduction of the CAR Δ1 pool. The indicated cells were transduced with AdCMV-GFP at an MOI of 20 and analyzed by flow cytometry as described in FIG. 1.

FIG. 6A shows CAR Δ1 expression in transgenic mice T-cells and FIG. 6B shows CAR Δ1 expression in transgenic B-cells.

DETAILED DESCRIPTION OF THE INVENTION

Figure 1:
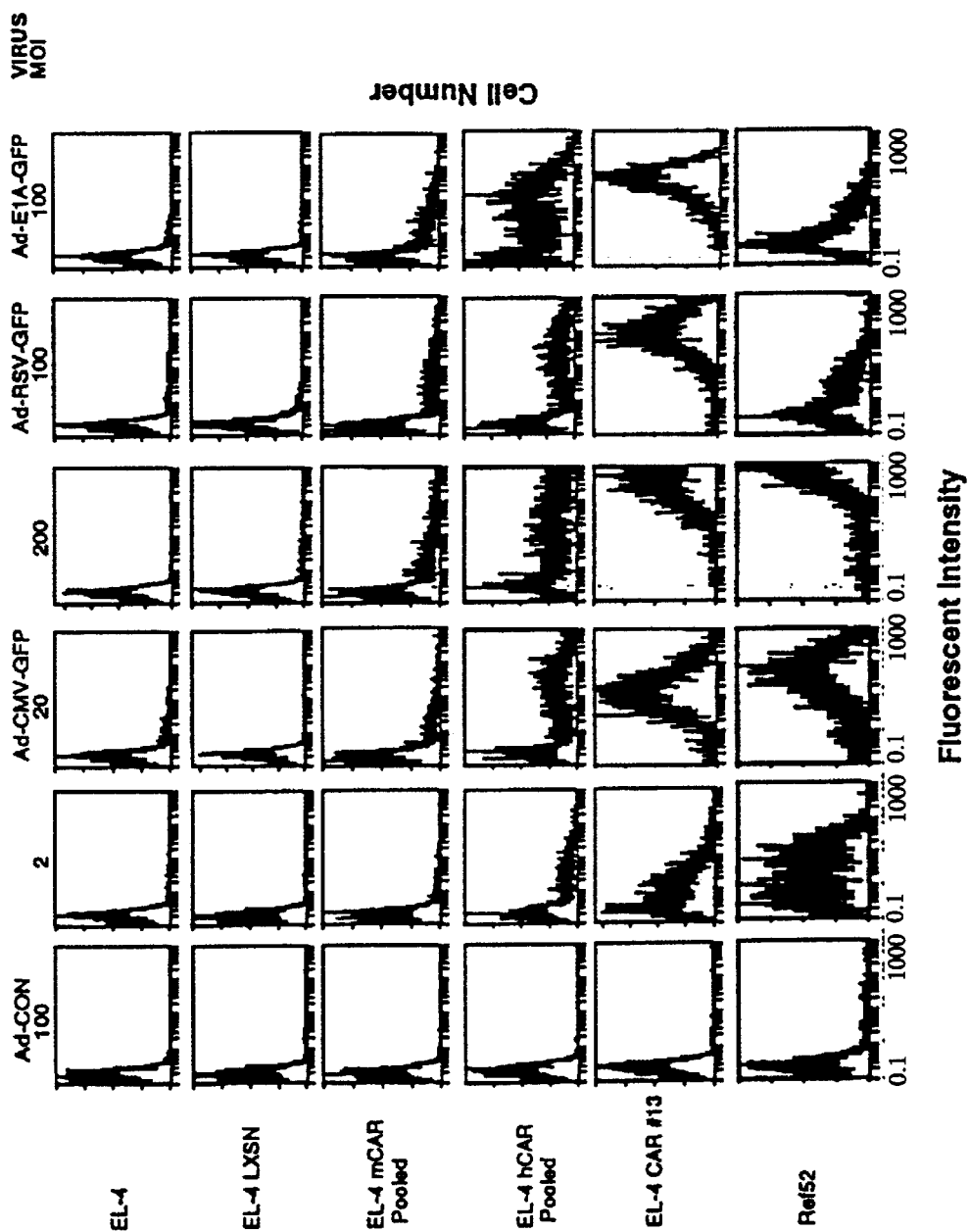
FIG. 1 shows that the expression of CAR in EL-4 cells confers susceptibility to adenovirus transduction. The indicated cells were transduced with the indicated MOI of either control adenovirus (Ad-CON) or with an adenovirus expressing green fluorescent protein (GFP) from either a Cytomegalovirus (CMV), Rous Sarcoma Virus (RSV) or Adenovirus Early Gene Product (E1A) promoter. After 24 hours, the live cells were analyzed by flow cytometry for the expression of GFP, as indicated by increased fluorescent intensity.

As used in the present invention, the following terms are defined as follows:

"Lymphocytes" refer to cells derived from the immune system, i.e., T and B cells. Lymphocytes used herein are cells isolated from transgenic mouse tissues or cells maintained as tissue culture cell line under standard conditions known in the art.

The term "vector" refers to a nucleic acid molecule capable of transporting another nucleic acid to which it has been linked. One type of vector is a "viral vector," wherein additional DNA segments can be ligated into a viral genome; other types of vectors include plasmids and yeast artificial chromosomes. Certain vectors, for example, retrovirus vectors, are integrated into the genome of a host cell upon introduction into the host cell, and thereby replicated along with the host genome. Moreover, certain vectors are capable of directing the expression of genes to which they are operatively linked. Such vectors are referred to herein as "expression vectors."

The "expression vectors" of the invention comprise a nucleic acid encoding a gene of interest in a form suitable for expression of the nucleic acid in a host cell, which means that the vectors include one or more regulatory sequences, selected on the basis of the host cells to be used for expression. The term "regulatory sequences" is intended to include promoters, enhancers, transcription termination signals, polyadenylation sequences, and other expression control elements. Regulatory sequences referred to in the invention include those which direct expression of the nucleic acid sequence only in certain host cells (e.g. tissue specific regulatory sequences such as the lymphocyte-specific IckB/CD2 promoter and enhancer combination).

The term "transduction" refers to a method of introducing viral DNA within a virus particle into a host cell. The viral DNA herein is in the form of recombinant virus, which is generated by linking a segment of DNA of interest to the viral genome in such a way that the gene can be expressed as a functional protein.

"MOI" stands for multiplicity of infection, which refers to the ratio of number of virus particles to number of host cells.

"Transgene" refers to a gene which is not part of native genetic material in a cell. Included in this definition is a coding sequence associated in nature with the organism, but operably linked to regulatory sequences with which it is not associated in nature. A "transgenic mouse" refers to a mouse which contains a segment of DNA that is not part of mouse genome in nature.

"Truncated CAR" (tCAR) used herein refers to a coxsackievirus and adenovirus receptor polypeptide with shorter carboxy terminal tail than a full-length CAR. A tCAR of the present invention comprises the extracellular and transmembrane domains of CAR, but lacks the portion of the cytoplasmic domain which results in upregulation of integrin synthesis in cells expressing the tCAR transgene.

The present invention is based on the discovery that the expression of the truncated CAR in lymphocytes is sufficient to confer full susceptibility of lymphocytes to adenovirus transduction. The absence of the cytoplasmic domain of the CAR protein confers the unexpected advantage that integrin expression in lymphocytes is not up-regulated. By contrast, expression of full-length CAR in lymphocytes results in increased integrin expression levels.

Previous studies have demonstrated that delivery of recombinant genes via adenoviruses to lymphocytes, either in vivo or in cell culture is inefficient. To examine the extent to which the EL-4 mouse thymoma cell line could be transduced with adenovirus, the cells were infected with either a control recombinant adenovirus (Ad-CON) or recombinant viruses that express the Green Fluorescent Protein (GFP) from either the Cytomegalovirus (CMV), Rous Sarcoma Virus (RSV) or E1A promoters (AdCMV-GFP, AdRSV-GFP or AdE1A-GFP respectively). As shown in FIG. 1, transduction of EL-4 cells with high multiplicities of infection (MOI) of these viruses failed to result in the expression of GFP in these cells, as measured by flow cytometry. In contrast, transduction of the rat embryo fibroblast cell line (Ref52) with AdCMV-GFP at MOIs of 20 or 200 resulted in the transduction of the entire population of cells, as evidenced by their bright fluorescence. Primary human foreskin fibroblast cells were transduced to a very similar extent as Ref52 cells. The next question tested was to see whether the expression of CAR would increase the susceptibility of EL-4 lymphocyte cells to adenovirus transduction. In order to facilitate the creation of lymphocyte cells lines that express CAR, LXSN retrovirus vectors were generated with either the mouse or human CAR coding sequences (from cDNA) determining full-length or truncated CAR. EL-4 cells were transduced either with the CAR-expressing retroviruses or the control retrovirus (LXSN) and then selected for neomycin resistance for 7–10 days. The pooled neomycin resistant populations were then transduced with Ad-CON or AdCMV-GFP-GFP at three different MOIs and analyzed by flow cytometry (FIG. 1). 71.6% of the EL-4 cells expressing the human CAR coding sequence and transduced with Ad-CMV-GFP (MOI of 200) were positive for GFP expression as seen by increased fluorescence. Since the expression of the mouse CAR coding sequence facilitated transduction by adenovirus to a lesser extent than human CAR (FIG. 1), all subsequent data presented are derived from human CAR-expressing cells.

CAR-expressing EL-4 cells were subsequently transduced with AdCMV-GFP (MOI of 20) and then single cell sorted for cells that displayed high fluorescence (fluorescent intensity ranging from 30 to 300). 14 single cell clones were expanded, and then retested for their susceptibility to adenoviral transduction. Similar results were observed for all tested clones. As seen in FIG. 1, transduction of the EL-4-CAR #13 clone with various multiplicities of AdCMV-GFP resulted in nearly 100% of the cells that exhibited high fluorescence, indicating successful delivery of GFP to almost all the cells. In fact, the EL-4 CAR #13 cells were as infectable as the highly susceptible fibroblast cells over the range of tested MOIs. AdRSV-GFP and AdE1A-GFP, while poorly expressed in the fibroblast cells, efficiently transduced and were expressed in the EL-4-CAR #13 cells, demonstrating the utility of recombinant adenoviruses that use these promoters for the expression of transgenes in lymphocytes.

Next, the cell surface expression of CAR was measured by flow cytometry of living cells following staining with the RmcB monoclonal [Hsu, K.-H. L. et al., (1988) *Journal of Virology* 62:1647–1652] against CAR (FIG. 2) and a FITC labeled goat anti-mouse IgG1 antibody. While EL-4 cells do not express detectable CAR, Ref52 fibroblast cells exhibit significant CAR expression, consistent with their high susceptibility to adenovirus infection. The pooled neomycin resistant EL-4 CAR cells showed variable expression of CAR, over approximately two logs of fluorescence intensity, consistent with their intermediate susceptibility to adenovirus. In contrast, the cloned and highly infectable EL-4 CAR #13 cells exhibited high level, uniform expression of cell surface CAR.

Figure 3:
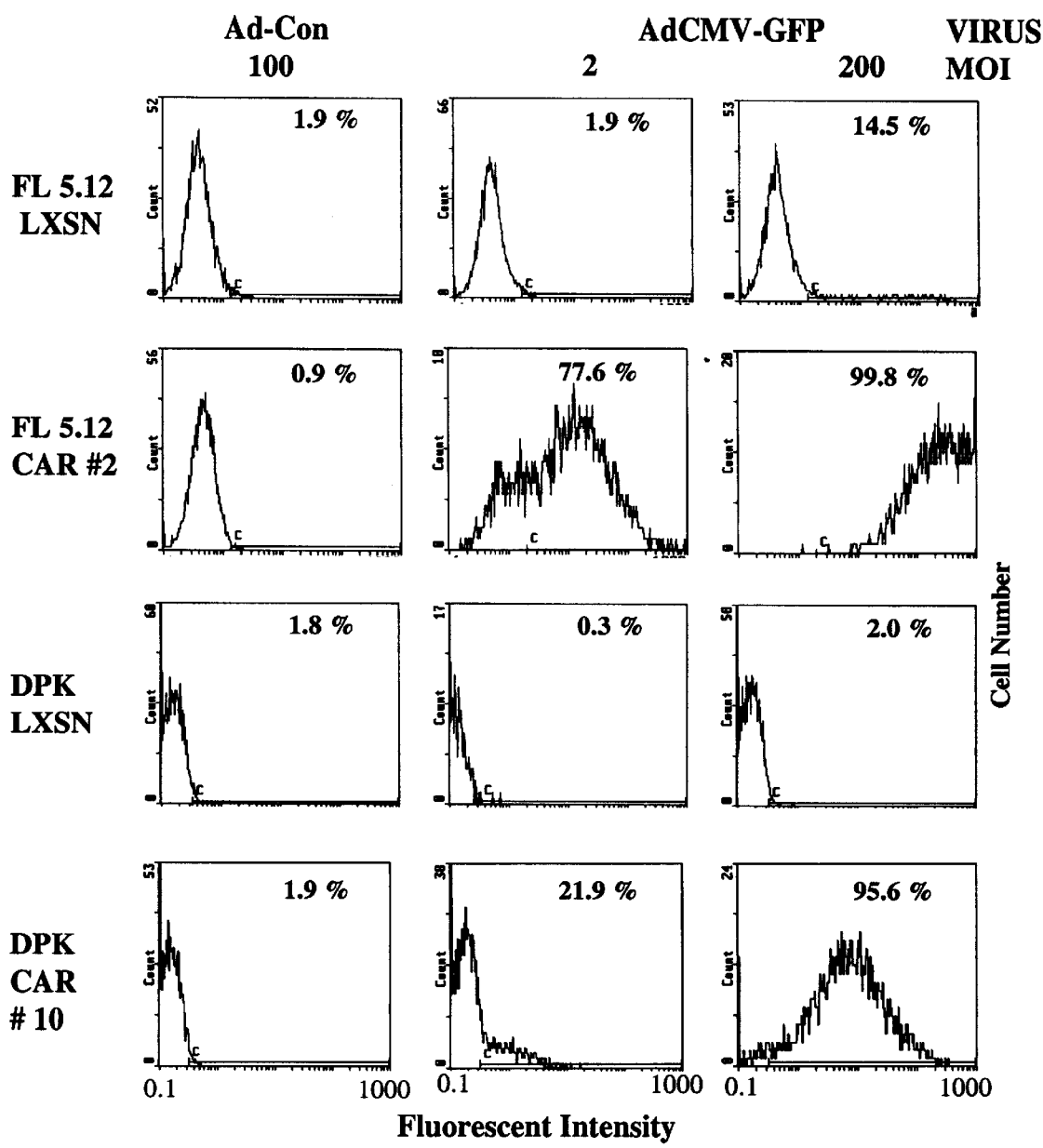
FIG. 3 demonstrates that CAR expression can facilitate adenovirus transduction of other lymphocyte cell lines. FL5.12, DPK.67, and the CAR expressing derivatives of these cell lines were transduced with either Ad-CON or AdCMV-GFP at the indicated multiplicity of infection (MOI) and analyzed by flow cytometry, as described in FIG. 1.

The above results clearly show that the expression of CAR in the EL-4 lymphocyte cell line conferred susceptibility to adenoviral transduction. Several other clonal lymphocyte cell lines that express the human CAR cDNA were also generated by the same procedure described above. Multiple cloned lines were generated for each cell line, and very similar results were obtained for all the clones. The cell lines used were the FL5.12 mouse IL-3 dependent pro-B cell line [McKearn, J. P. et al., (1985) *Proc. Natl. Acad. Sci.* 82:7414–7418] and the DPK.C7 mouse thymoma line from the AND transgenic mouse [Kaye, J. et al., (1992) *Cell* 71:423; Kovalik, J. et al., (1996) *JI* 157:5290–5299]. As shown in FIG. 3 the LXSN-transduced populations of FL5.12 and DPK.C7 cells were poorly transduced by AdCMV-GFP. In contrast, clones of these cells that express CAR were very efficiently (ca. 100%) transduced by AdCMV-GFP. These results demonstrate that the expression of CAR facilitates the transduction of both B and T cell lines. Recent experiments indicate that CAR can also facilitate adenoviral gene transfer in the Ba/F3 IL3-dependent pre-B cell and mouse 32DC13 pre-myeloid cell lines.

Figure 2:
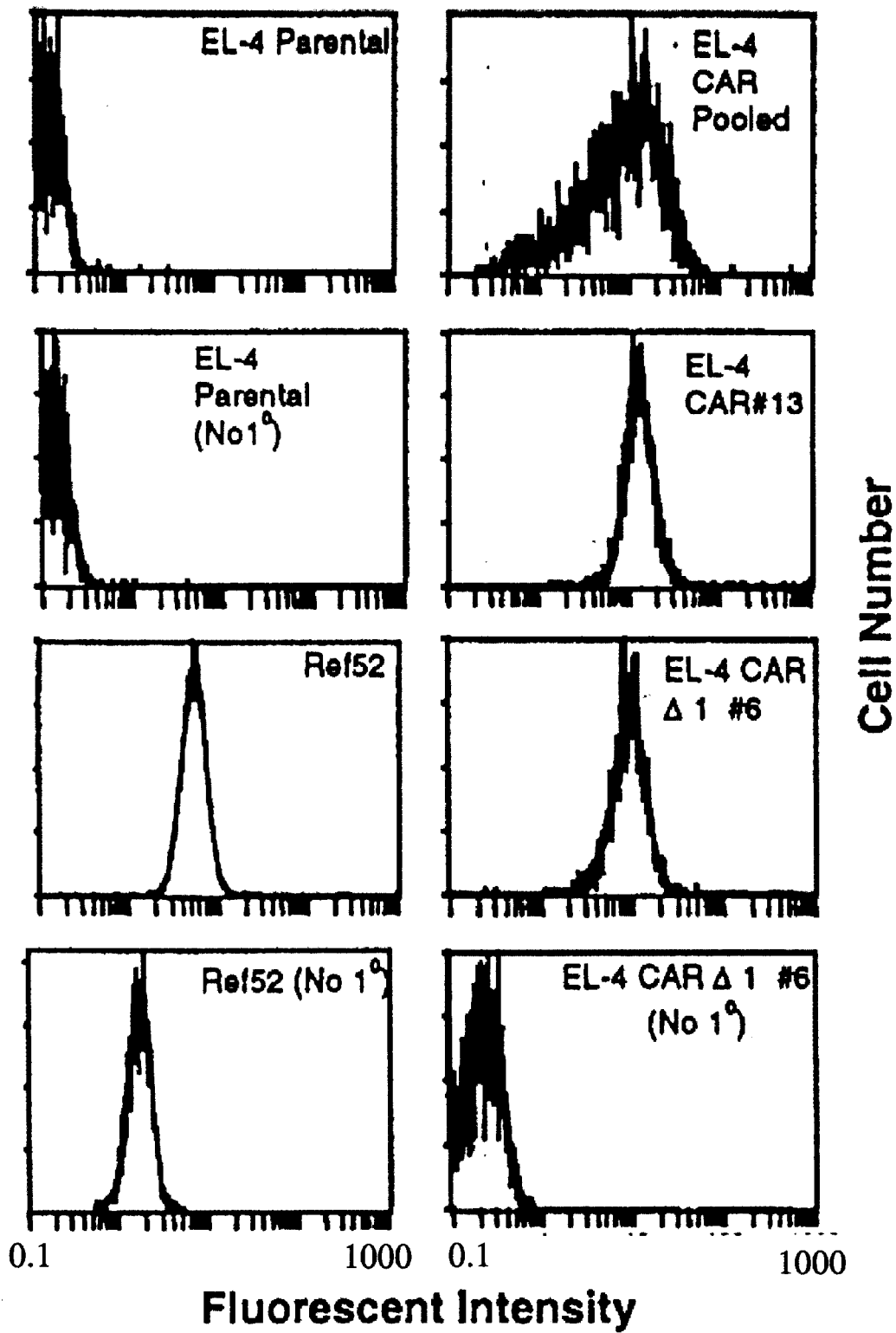
FIG. 2 shows analysis of cell surface expression of CAR. The expression of CAR was determined on the indicated cells by incubation of the cells with a RmcB monoclonal antibody specific for CAR (or no primary antibody as a control) followed by incubation with FITC-linked goat a-mouse IgG1 antibody.
Figure 4B:
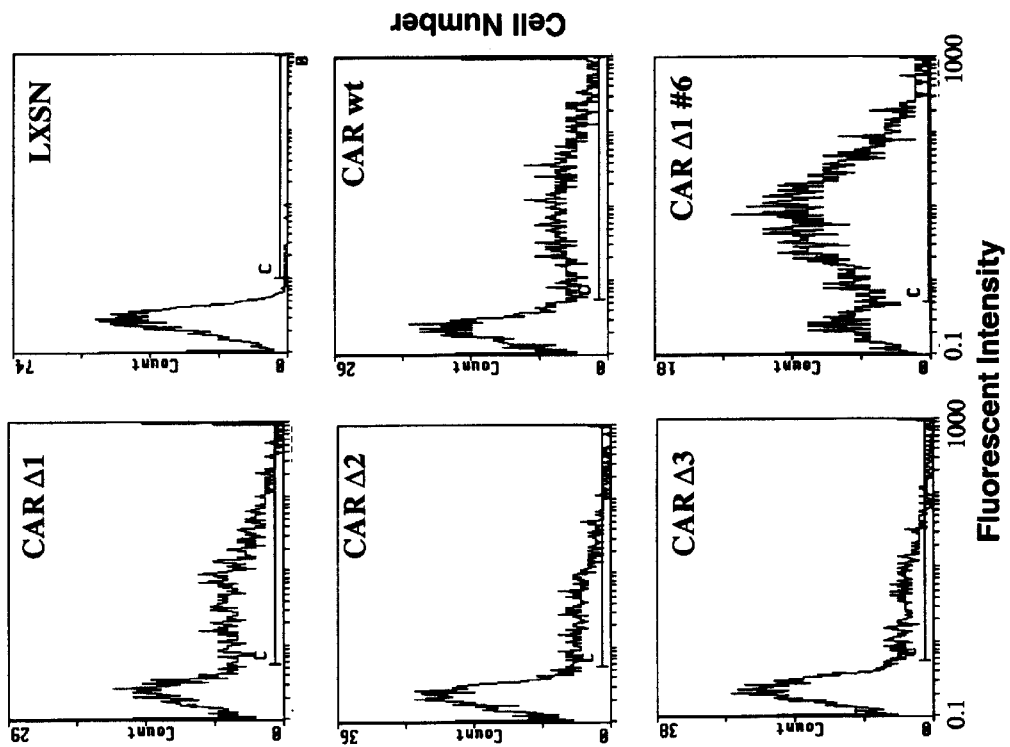
FIGS. 4A and 4B show that the cytoplasmic domain of CAR is not required to facilitate adenovirus transduction.
Figure 4A:
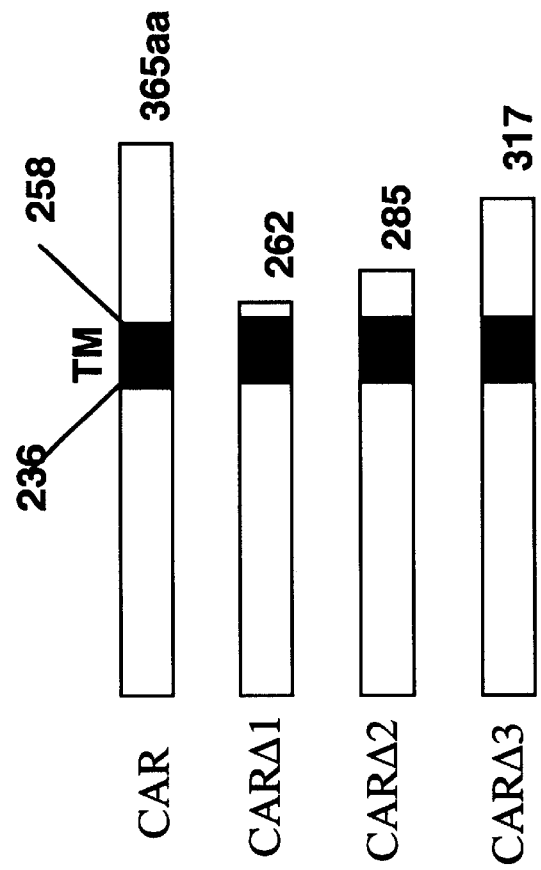

Given that the expression of CAR facilitated adenoviral transduction of lymphoid cell lines, the regions of the CAR protein that are required for facilitating virus entry were next determined. Although the cytoplasmic domain of the cellular receptor for certain viruses might be required to mediate viral entry, in the case of group C adenovirus, the integrin component of the receptor complex may be sufficient to mediate internalization by endocytosis via clathrin coated pits. Therefore CAR deletion mutants were generated from the C-terminal cytoplasmic region, and they were expressed via retroviral vectors in EL-4 cells (FIG. 4A). As shown in FIG. 4B, all three CAR constructs with deletions of C terminal sequence conferred adenoviral susceptibility to EL-4 cells to an extent similar to that for the full length CAR. A single cell-derived clonal line from CAR Δ1, which encodes a protein with only four amino acids C-terminal to the predicted transmembrane domain was generated, and all recombinant cells were very efficiently transduced with AdCMV-GFP (FIG. 4B). CAR Δ1 was expressed on the cell surface at levels similar to full length CAR, as demonstrated by flow cytometric analysis of cells stained with the RmcB monoclonal (FIG. 2). Therefore, the cytoplasmic domain of CAR is not required for adenovirus transduction. This suggests that the role of CAR is primarily as a docking protein for the adenovirus fiber protein, and that the interaction of the viral penton base proteins with the cellular integrins mediates internalization.

Figure 5:
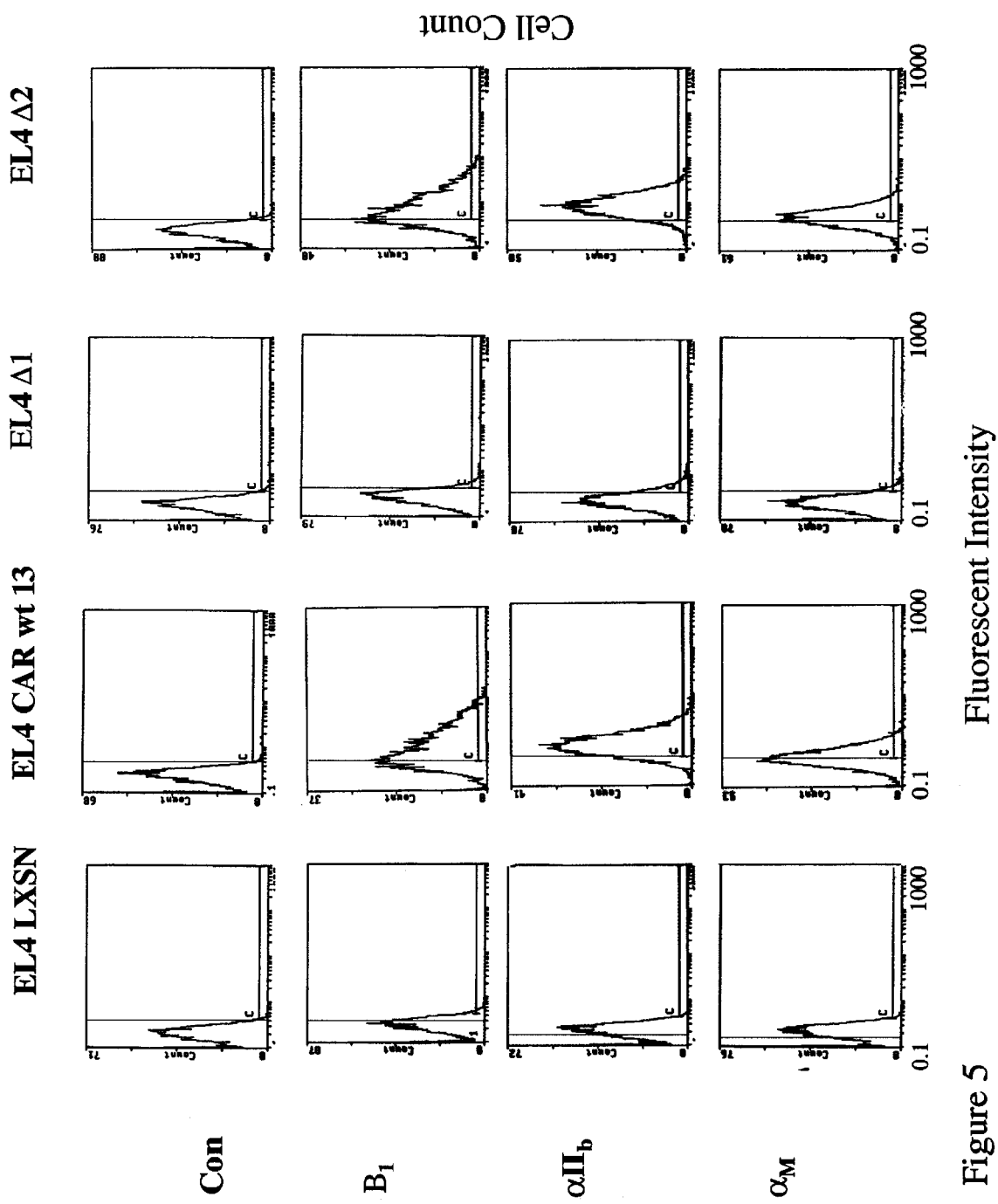
FIG. 5 shows the expression profile of the integrins, β1, αIIb or αM, in EL-4 cells expressing the indicated CAR gene. Results were obtained using specific antibodies for the given integrins, followed by flow cytometric analysis.

That the cytoplasmic domain of CAR is dispensable for virus transduction not only contributes to our understanding of virus entry, but from a practical standpoint, CAR Δ1 appears attenuated in its normal function in the cell, and it appears to exert less of an effect on cell physiology. This is particularly important given the absence of any obvious catalytic domains in the cytoplasmic domain of CAR, and a lack of understanding of the normal cellular role of the CAR protein. In fact, as shown in FIG. 5, the expression of full-length CAR, but importantly not CAR Δ1, upregulates the expression of various integrins on EL-4 thymoma cells (an established T cell line). Interestingly CAR Δ2, which possesses 23 additional amino acids C-terminal to CAR Δ1, upregulates the integrin expression, indicating that certain residues between 262 to 286 are required for this effect. Integrins are essential for various aspects of lymphocyte physiology, including the attachment of activated lymphocytes to vesicle endothelial cells during migration to a site of inflammation. Activated T cells show upregulated expression of various integrins, which is required for homing to sites of infection. Without wishing to be bound by any particular theory, it is believed that the upregulation of integrin expression by the expression of full length CAR substantially disrupts normal lymphocyte physiology (i.e. CAR-expressing T cells may invade tissues in the absence of inflammation). CAR Δ1 does not affect integrin expression and yet fully confers adenoviral transduction. Thus, the CAR Δ1-expressing lymphocytes are useful for in vivo and ex vivo studies using adenoviral gene delivery. The C-terminal boundary for a CAR deletion mutant can include residues between 259 and 284, with reference to SEQ ID NO:2, provided that integrin expression is not upregulated.

Figure 6A:
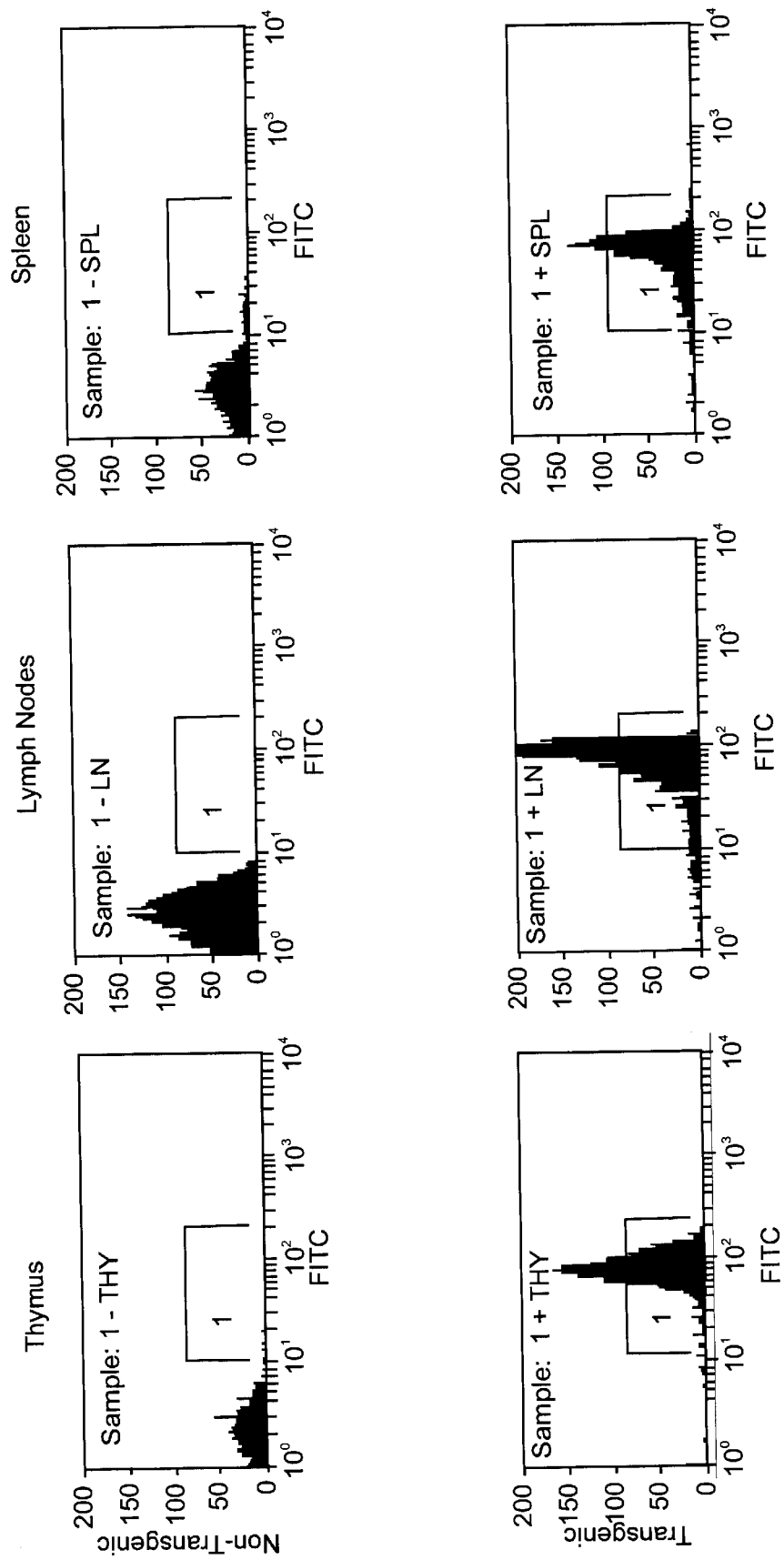
FIGS. 6A and 6B show flow cytometric analysis of CAR expression: Lymphocytes were isolated from either the lymph nodes, spleen or thymus of transgenic or non-transgenic mice. $10^6$ cells were incubated with a 1:100 dilution in 5% FBS in PBS of CAR-reactive RmcB monoclonal ascites fluid for 45 min on ice. The cells were washed twice with PBS, and incubated with a 1:100 dilution of FITC labeled Goat anti-mouse IgG1 (PharMingen #02234D, San Diego, Calif.) for 45 min on ice. The cells were subsequently stained by the B cell specific antibody to B220 and a T cell specific antibody to CD3. The cells were washed twice with PBS and analyzed by flow cytometry. Cells were first gated for either B220 (B cells) or CD3 (T cells) expression, and then analyzed for the expression of CAR (increased FITC signal).
Figure 6B:
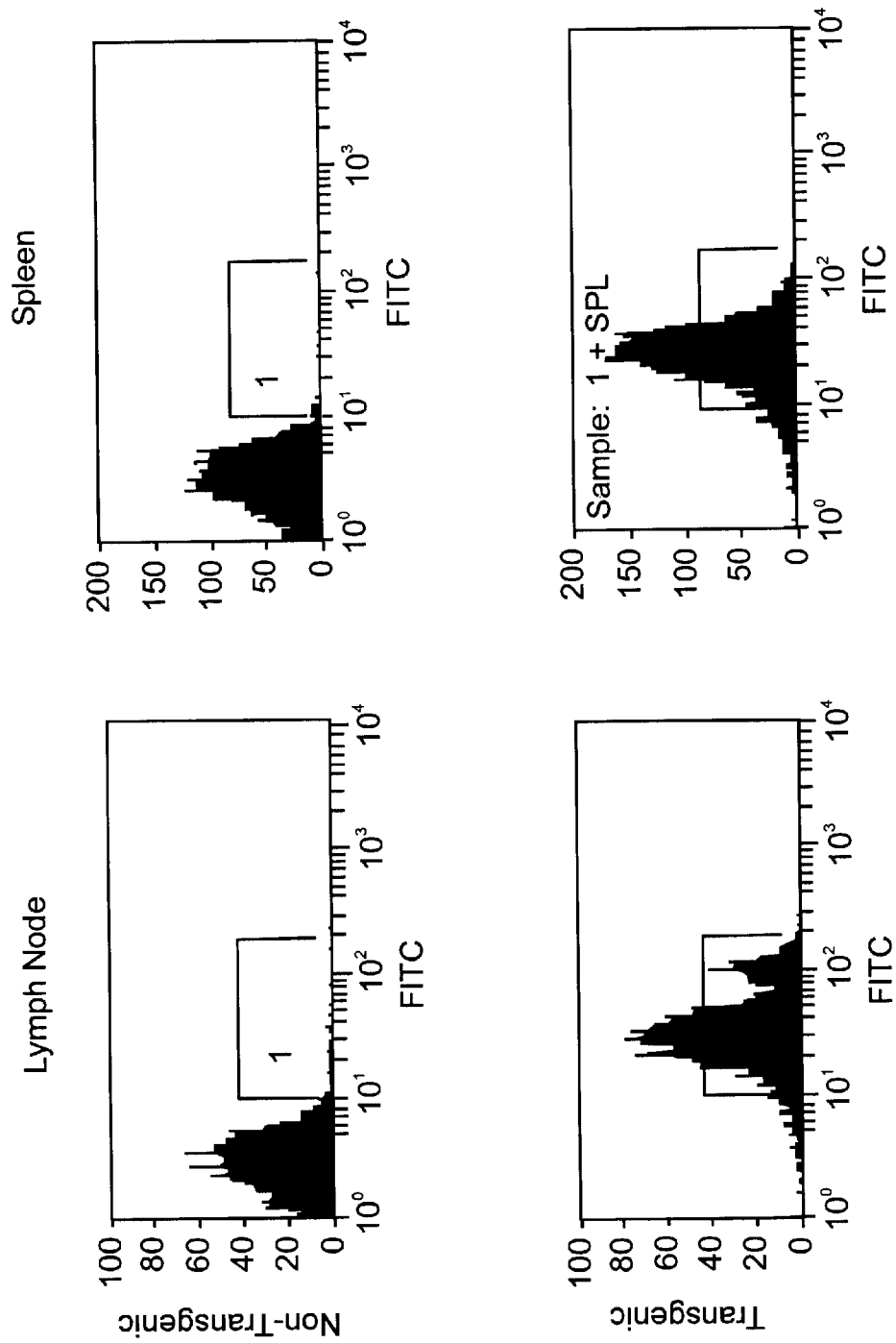
Figure 7B:
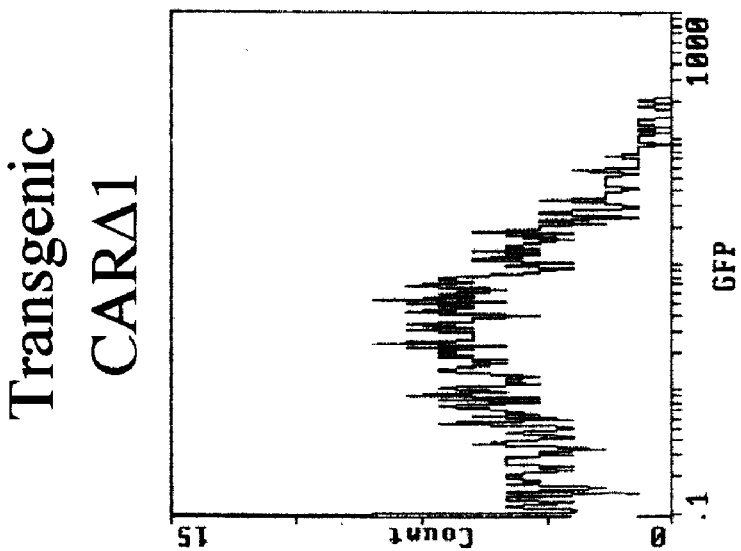
FIG. 7A and 7B demonstrate infection of lymphocytes derived from non-transgenic control and CAR Δ1. The thymus was removed from the indicated animals, and $1 \times 10^8$ T-cells per mL were infected with AdCMV-GFP virus at an MOI of 30 (in RPMI 2% FBS, total volume of 50 λ). After a 1 hour infection at 37° C., the cells were placed in a total volume of 1 mL RPMI, 10% FBS and incubated 18 hours at 37° C. The samples were then removed, centrifuged, and resuspended in 500 λ PBS, and GFP fluorescence was analyzed by flow cytometry.
Figure 7A:
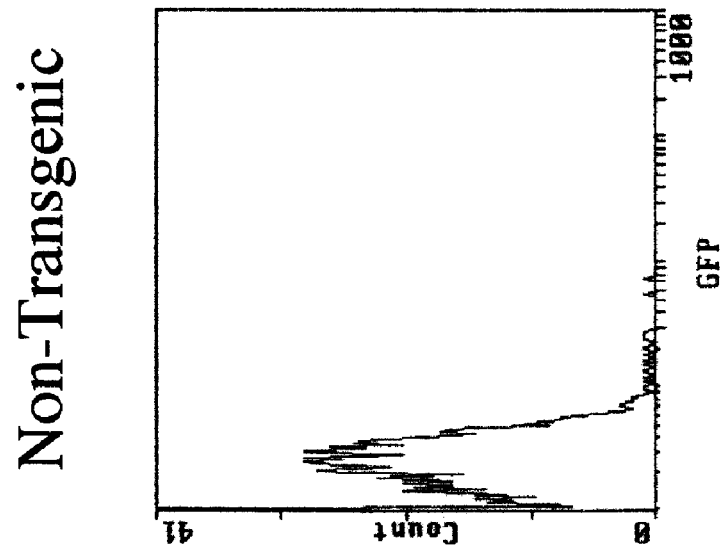

In addition to allowing gene transfer into lymphocyte cell lines, the expression of CAR in mice can facilitate gene transfer either in vivo or ex vivo in primary cell culture. Transgenic mice were generated that express CAR Δ1 from the proximal Lck promoter/human CD2 enhancer, which directs expression primarily in lymphocytes (FIGS. 6A and 6B). As shown in FIG. 7B, the expression of CAR Δ1 on T cells allows for the efficient transduction of these cells with Ad-GFP. CAR Δ1 transgenic mice are also created wherein CAR Δ1 is expressed from the human CD2 minigene, containing locus control regions that reduce position effect variegation of transgene expression. Expression is restricted to T cells. CAR transgenic mice facilitates either the in vivo delivery of genes into T cells by the inoculation of adenovirus recombinants into lymphoid organs and the ex vivo delivery of genes into transgenic T cells followed by their introduction into a recipient mouse. This is a major advancement in the field in view of the limitations of the prior art technologies. Lymphocyte that express CAR are valuable for the analysis of pathways, via gene transfer, which control various aspects of cellular physiology either in vitro or in vivo.

A particular advantage of adenoviral-mediated gene delivery is the ability to efficiently express genes whose products have activities, such as the induction of apoptosis, that are incompatible with long term expression. The binding of Fas ligand (FasL) to its receptor, FasR, results in the recruitment of FADD via the death domain of FasR, followed by the activation of a caspase cascade and apoptosis [Nagata, S. (1997) Cell 88:355–365]. While expression of FasL together with FasR can contribute to the death of a cell, the expression of FasL alone can confer on a cell the license to kill, which contributes to target killing by cytotoxic T cells as well as immune privilege of certain tissues such as the eye and testis. In order to study the ability of FasL-expressing cells to kill FasR-expressing targets, a recombinant adenovirus was created that encodes FasL (Ad-FasL). Because expression of FasL in 293 cells induces apoptosis, the Ad-FasL was generated by using 293 cells that over express the caspase inhibitor CrmA.

Figure 8:
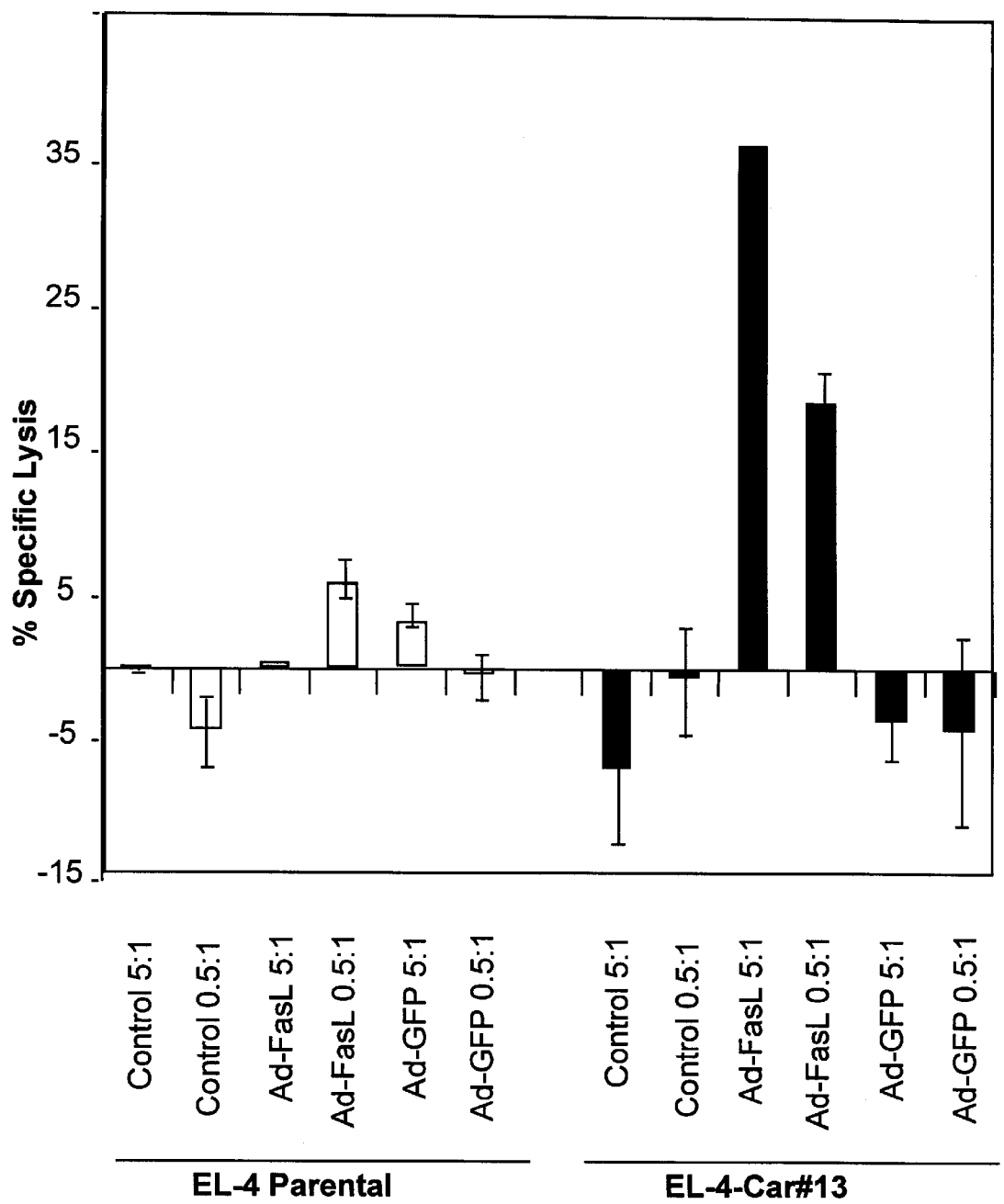
FIG. 8 demonstrates that EL-4-CAR cells transduced with an adenoviral FasL effectively kill FasR-expressing target cells. EL-4-CAR #13 cells were transduced (MOI of 100) with Ad-FasL, ADCMV-GFP, or no virus (control). The cells were then washed once, and coincubated for 20 hr with $^{51}$Cr-labeled L1210-FasR cells at a 5:1 or 0.5:1 effector:target ratio. Each value represents the mean of triplicate measurements±standard deviation.

To test the ability of the CAR-expressing EL-4 cells to express FasL encoded by an adenovirus construct, a standard cytoxicity assay was employed. The lymphocytic cell line L1210-FasR was chosen as a target cell line since it stably expresses high levels of FasR and readily undergoes apoptosis in response to FasL [Rouvier, E., et al., (1998) Journal of Experimental Medicine 177:195–200]. L1210-FasR were radiolabeled with chromium 51 ($^{51}Cr$), incubated with various ratios of FasL-expressing cells, and apoptosis was quantitated based on the release of $^{51}Cr$ from the cells into the supernatant. As shown in FIG. 8, parental EL-4 cells were unable to induce FasR -mediated death regardless of whether they were exposed to Ad-FasL. In contrast, El-4-CAR #13 that were transduced with Ad-FasL killed L1210-FasRE cells in a dose-dependent manner, lysing 37% of the cells at a 5:1 effector to target ratio. This result indicates that the expression of FasL by E1-4 cells mediates cell killing of FasR-expressing target cells. This effect was specific for FasL since untransduced and Ad-CMV-GFP transduced E1-4-CAR cells failed to induce apoptosis. These data demonstrate a functional application of CAR expressing lymphocytes in the analysis of apoptotic pathways.

Expression of truncated CAR in lymphocyte cells confers susceptibility to adenoviral transduction. The availability of CAR-expressing lymphocyte cells facilitates molecular analyses of pathways affecting lymphocyte function, as well as gene therapy. Since the entire cell population can be transduced, the effect of the introduced gene product on endogenous biochemical activities can be easily measured. In contrast, retrovirus vectors which are currently used for gene delivery into lymphocyte cells, can transduce only a fraction of the cells during mitosis. A further advantage of CAR expressing lymphocyte cells is that multiple gene products can be introduced by cotransduction with different adenoviral recombinant viruses, and expression levels can be manipulated by varying the MOIs. In addition, this system avoids the need for clonal expansion, and thus allows one to express and compare the activities of different gene products in identical populations of cells.

Expression of CAR in lymphocyte cells in mice facilitates gene transfer either in vivo or ex vivo in primary cell culture. For example, one can study the function and regulation of the immune system by inoculating adenovirus recombinants containing suspected regulatory genes into the thymus or lymph nodes.

Monoclonal or polyclonal antibodies, preferably monoclonal, specifically reacting with a tCAR encoded by a particular coding sequence may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol*. 218, Part I; Wu (ed.) (1979) *Meth Enzymol*. 68; Wu et al. (eds.) (1983) *Meth. Enzymol*. 100 and 101; Grossman and Moldave (eds.) *Meth. Enzymol*. 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, N.Y. Abbreviations and nomenclature, where employed, are deemed standard in the field and commonly used in professional journals such as those cited herein.

All references cited in the present application are incorporated by reference herein to the extent that they are not inconsistent with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLE 1

Construction of Plasmids

The LXSN-hCAR and LXSN-mCAR plasmids were generated by ligation of the EcoRI/XhoI cDNA fragments from either hCAR-pcDNA1-strider or pCMV-Sport2-mCAR [Bergelson et al. (1998) *J. Virol.* 72:415–419] into EcoRI/XhoI digested LXSN.Vec1 [Miller et al. (1989) *Biotechniques* 7:980–988]. Deletion mutations of hCAR were created by 25 cycles of PCR amplification of LXSN-hCAR with the following primers:

5' GAATTCCCAGGAGCGAGAGCC 3' (SEQ ID NO:3) with either

5' GCAGCTCGAGCTATTTACGACAGCAAAAGATGAT 3' (Δ1) (SEQ ID NO:6),

5' GCAGCTCGAGCTACACATCTTCCCTGATATCGTG 3' (Δ2) (SEQ ID NO:4),

5' GCAGCTCGAGCTATCCTTCCATGTTGGAAGG 3' (Δ3) (SEQ ID NO:5).

The resulting PCR products were digested with EcoR1/Xho (sites in the primers) and cloned into EcoRI/XhoI digested LXSN.Vec1. Deletion mutations of mCAR can be created similarly using mouse CAR sequence specific primers.

EXAMPLE 2

Cells and Virus

EL-4 and DPK.C7 cells were grown in RP10 (10% FBS in RPMI 1640 with 0.1 mM 2-mercaptoethanol and 1% penicillin-streptomycin (P/S) (Gibco/BRL, Gaithersburg, Md.). FL5.12 cells were grown in RP10 supplemented with 20% filtered WEHI conditioned media. The Ref52 fibroblasts were grown in 5% FBS, 5% CS and 1% P/S in DMEM, and the phoenix 293-T amphotropic producer cell line was grown in 10% FBS and 1% P/S in DMEM (DME10). The LXSN plasmids were transfected by standard calcium-phosphate procedures into Phoenix 293 producer cell line (in DME10) as described previously [Pear, W. S. et al., (1993) *Proc. Natl. Acad. Sci. USA* 90:8392–8396], the media changed after 16 hours to 10% FBS and 1% P/S in ΔMEM (MEM10), and the LXSN retrovirus-containing supernatant was harvested after 2 days and filtered through a 0.2 micron filter. $2 \times 10^6$ cells were infected with 4 mls of this supernatant for 4 hrs with 4 ug/ml hexadimethrine bromide (Polybrene, Trademark of Abbott Laboratories, Chicago, Ill.), and then 16 mls of MEM10 was added. The next morning, the cells were changed to RP10. For FL5.12 cells, the media was supplemented with 20% WEHI throughout. Two days later, the cells were cultured in RP10 with 0.5 mg/ml G 418 (Geneticin Gibco/BRL), and pooled G418 resistant cells were obtained after about 1 week.

Cells were transduced with adenovirus in their standard growth media but with 2% serum at $10^7$ cells per ml for 320 min at room temperature. Complete media was then added to the transduced cells (final density of $r \times 10^5$ cells/ml) and the cells were incubated 24 hrs at 37° C. The cells were then washed once with BPS, and analyzed on a Coulter Epics XL flow cytometer. For the isolation of single cell clones, the cells were sorted into 96 well plates on the MoFlo from Cytomation. Adenoviruses were purified by CsCl gradient centrifugation and virus titers were determined by an indirect immunofluorescence assay using an antibody against E2A (72K) as described previously [Nevins et al., (1997) supra]. The construction of Ad-FasL and the GFP expressing viruses is described previously [Hedlund et al., (1999) *Cell Death and Differentiation* 6:175–182].

EXAMPLE 3

Flow Cytometric Analysis for CAR Expression $10^6$ cells were incubated with a 1:100 dilution in 5% FBS in PBSD of RmcB monoclonal ascites fluid for 45 min on ice [Bergelson et al., (1998) *J. Virol* 72:415–419]. The cells were washed twice with PBS, and incubated with a 1:100 dilution of FITC labeled Goat anti-mouse IgG1 (PharMingen, San Diego, Calif., #02234D) for 45 min on ice. The cells were washed twice with PBS and analyzed by flow cytometry.

EXAMPLE 4

Cell Killing Assays

EL-4-CAR #13 or EL-4 parental cells were transduced as described above with AdCMV-GFP, Ad-FasL, or no virus (control) in RP10. 118 hours post transduction the cells were washed twice and 100 μl containing $2.5 \times 10^4$ cells (5:1 effector:target (E:T) ratio) or 2500 cells (0.5:1 E:T ratio) were added in triplicate to a 96-well V-bottom plate. The target cell line L1210-FasR was labeled with 100 μCi $^{51}$Cr per $2 \times 10^6$ cells as described previously [Duke, R. et al., (1983) *Proc. Natl. Acad. Sci. USA* 80:6361–6365]. After washing 3 times, 5000 labeled cells in 100 μl were added per well to the various effector cells. Maximum lysis (100%) was determined by adding 100 μl medium. The 96-well plate was briefly centrifuged at 500 rpm, and incubated for 24 h. The plate was recentrifuged prior to removing 100 μl supernatant from each well for gamma counting.

EXAMPLE 5

Generation of CAR Transgenic Mice

The CAR Δ1 cDNAs were cloned into either the 1ckB/CD2 enhancer transgenic construct or the CD2 minigene transgenic construct by standard recombinant DNA techniques [Smith et al. (1996) *EMBO J.* 15(19):5167–5176; Chaffin et al. (1990) *EMBO J.* 9:3821–3829]. Plasmid constructs were verified by restriction enzyme digestion, and the plasmids were prepared by CsCl gradient centrifugation. To create transgenic mice, the construct DNAs were injected into the pronucleus of one-cell embryos from FVB/N mice. The detailed description of this technology can be found in Hogan et al. (1994) *Manipulating the Mouse Embryo, A Laboratory Manual,* Second Edition, Cold Spring Harbor Laboratory Press, Plainview, N.Y. This strain of mice was chosen because of the large pronuclei of its fertilized eggs and the production of large litters of pups. Female FVB/N mice were induced to superovulate by injection of pregnant mare's serum (PMS) followed by injection of human chorionic gonadotropin two days later. These females were mated with fertile males, and eggs were collected the next day from the oviducts and digested with hyaluronidase to remove the follicle cells. The eggs were then injected with the CAR Δ1 constructs and transferred into the oviducts of pseudopregnant female mice. Offspring were genotyped by the isolation of genomic DNA from tail biopsies, followed by Southern and PCR analysis using primers:

5' GAATTCCCAGGAGCGAGAGCC 3' (SEQ ID NO:3) and

5' CAGCTCGAGCTATTTACGACAGCAAAAGATGAT 3' (Δ1) (SEQ ID NO:6), and observing a characteristic amplification product of 821 bp for the presence of transgene DNA.

Mice that were positive for the transgene DNA were then analyzed for the expression of CAR Δ1 in lymphocytes. Blood (ca. 50 microliters) was obtained from the subocular vesicle bed, and red blood cells were lysed using hemolytic buffer. The remaining lymphocytes were then analyzed for the express of CAR by immunostaining with the RmcB monoclonal antibody followed by flow cytometry. Transgenic mice that exhibited lymphocytic expression of CAR Δ1 were then crossed to non-transgenic mice to generate additional transgenic offspring for each transgenic line.

EXAMPLE 6

Integrin Expression

Relative levels of integrin expression in CAR-expressing, tCAR-expressing and untransformed control cells are measured by the use of integrin-specific antibodies. All antibodies were purchased from PharMingen (San Diego, Calif.) and were used as per manufacturer's instructions.

What is claimed is:

1. A transgenic mouse whose genome comprises a transgene comprising a nucleotide sequence encoding a truncated Coxsackievirus and/or Adenovirus Receptor (tCAR) polypeptide operably linked to a lymphocyte-specific transcription regulatory nucleotide sequence, wherein said tCAR is expressed in the lymphocytes of said mouse at levels sufficient for increased susceptibility to adenoviral transduction of said lymphocytes without affecting the expression of endogenous integrins in said lymphocytes.

2. The transgenic mouse of claim 1, wherein said lymphocyte-specific transcription regulatory nucleotide sequence is a Lck promoter/human CD2 enhancer.

3. The transgenic mouse of claim 1, wherein said tCAR polypeptide is set forth in amino acids 1–262 of SEQ ID NO:2.

* * * * *

UNITED STATES PATENT AND TRADEMARK OFFICE
CERTIFICATE OF CORRECTION

PATENT NO.   : 6,245,966 B1                              Page 1 of 1
DATED        : June 12, 2001
INVENTOR(S)  : DeGregori It is certified that error appears in the above-identified patent and that said Letters Patent is hereby corrected as shown below:

Column 2,
Line 67, replace "a-mouse" with -- α-mouse --.

Column 9,
Line 18, replace
"5' GCAGCTCGAGCTATTTACGACAGCAAAAGATGAT 3' (Δ1) (SEQ ID NO:6)"
with -- 5' CGCAGCTCGAGCTATTTACGACAGCAAAAGATGAT 3' (Δ1)
(SEQ ID NO: 6) --.
Line 20, replace
"5' GCAGCTCGAGCTACACATCTTCCCTGATATCGTA 3' (Δ2) (SEQ ID NO: 4)"
with -- 5' CGCAGCTCGAGCTACACATCTTCCCTGATATCGTA 3' (Δ2)
(SEQ ID NO:4) --.
Line 22, replace
"5' GCAGCTCGAGCTATCCTTCCATGTTGGAAGG 3' (Δ3) (SEQ ID NO: 5)"
with -- 5' CGCAGCTCGAGCTATCCTTCCATGTTGGAAGG 3' (Δ3)
(SEQ ID NO:5) --.

Column 10,
Line 66, replace
"5' CAGCTCGAGCTATTTACGACAGCAAAAGATGAT 3' (Δ1) (SEQ ID NO:6)"
with -- 5' CGCAGCTCGAGCTATTTACGACAGCAAAAGATGAT 3' (Δ1)
(SEQ ID NO: 6) --.

Signed and Sealed this

Nineteenth Day of February, 2002

*Attest:*

*Attesting Officer*

JAMES E. ROGAN
*Director of the United States Patent and Trademark Office*